United States Patent [19]
Uhlendorf et al.

[11] Patent Number: 5,678,553
[45] Date of Patent: Oct. 21, 1997

[54] ULTRASONIC PROCESSES AND CIRCUITS FOR CARRYING OUT THOSE PROCESSES

[75] Inventors: Volkmar Uhlendorf; Christian Hoffmann; Thomas Fritzsch, all of Berlin, Germany

[73] Assignee: Schering Aktiengesellschaft, Berlin, Germany

[21] Appl. No.: 332,746

[22] Filed: Nov. 1, 1994

[51] Int. Cl.$^6$ .................................................. A61B 8/00
[52] U.S. Cl. ............................................... 128/662.02
[58] Field of Search ............ 128/660.07, 661.07–661.1, 128/662.02; 73/861.25

[56] References Cited

U.S. PATENT DOCUMENTS

| | | | |
|---|---|---|---|
| 3,640,271 | 2/1972 | Horton | 128/660.02 |
| 4,452,082 | 6/1984 | Miwa | 73/599 |
| 4,483,345 | 11/1984 | Miwa | 128/660.02 |
| 4,532,812 | 8/1985 | Birchak | 73/861.27 |
| 4,610,255 | 9/1986 | Shimura et al. | 128/662.02 |
| 5,195,520 | 3/1993 | Schlief et al. | 128/662.02 X |
| 5,255,683 | 10/1993 | Monaghan | 128/662.02 |
| 5,410,516 | 4/1995 | Uhlendorf et al. | 367/7 |
| 5,425,366 | 6/1995 | Reinhardt et al. | 128/662.02 |
| 5,456,257 | 10/1995 | Johnson et al. | 128/662.02 |
| 5,526,816 | 6/1996 | Arditi | 128/662.02 |
| 5,560,364 | 10/1996 | Porter | 128/662.02 |
| 5,567,415 | 10/1996 | Porter | 128/662.02 |
| 5,577,505 | 11/1996 | Broch-Fisher et al. | 128/662.02 |

OTHER PUBLICATIONS

Germain et al., "Generation and detection of high-order harmonics . . . ", J. Acoust. Soc. Am. 83(3), Mar. 1988, pp. 942–949.

Law et al., "Ultrasonic determination of the nonlinearity parameter . . . ", J. Acoust. Soc. Am. 69(4), Apr. 1981, pp. 1210–1212.

*Primary Examiner*—Francis Jaworski
*Attorney, Agent, or Firm*—Millen, White, Zelano, & Branigan, P.C.

[57] ABSTRACT

A process for selective graphic representation and/or evaluation of the Doppler spectrum of objects limitedly resistant to sonic intensity, for example biological organs and tissues, by an ultrasonic process wherein a material is introduced in the examination area to be acoustically irradiated, nonlinear oscillations are produced in the examination area by irradiated ultrasonic waves and the signal is evaluated by an ultrasonic converter. Also, a circuit for carrying out the above process is disclosed.

74 Claims, 13 Drawing Sheets

$f_0$ = 4.0 MHz, +15 dBm AT THE SOUND HEAD
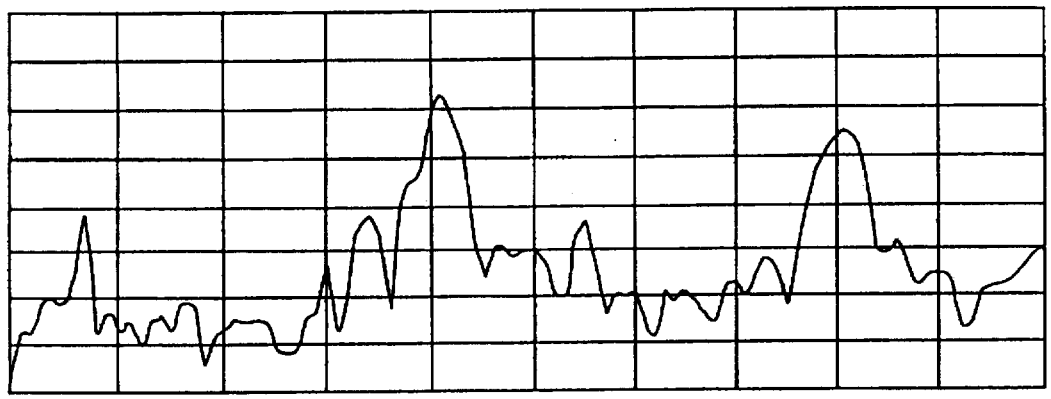
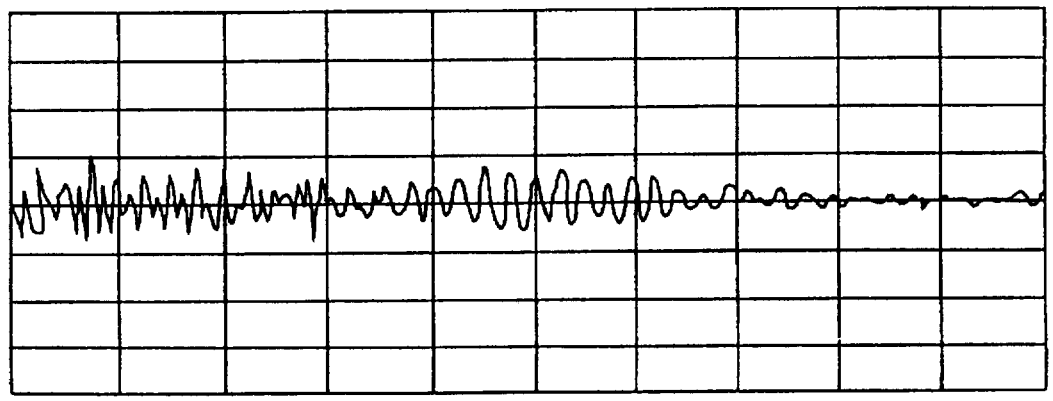
TIME
FIG. 6

$f_0 = 3.0$ MHz, +15 dBm AT THE SOUND HEAD
$2_0 \times f$   $3_0 \times f$
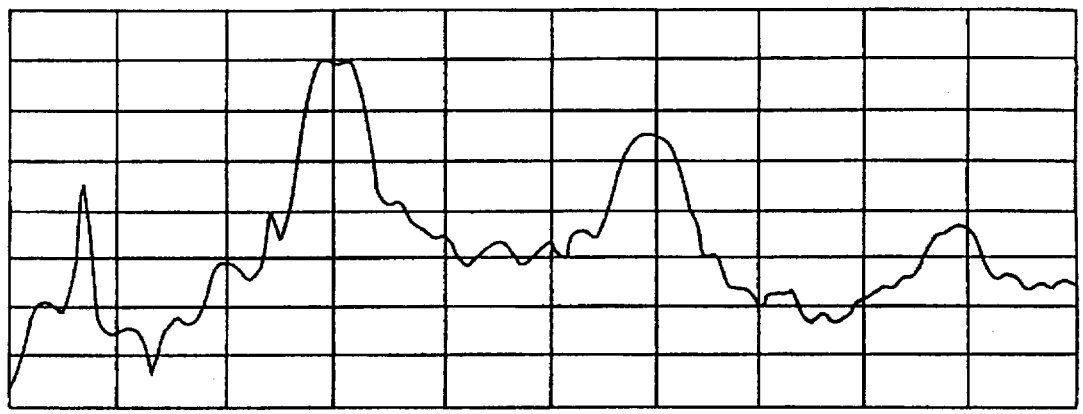
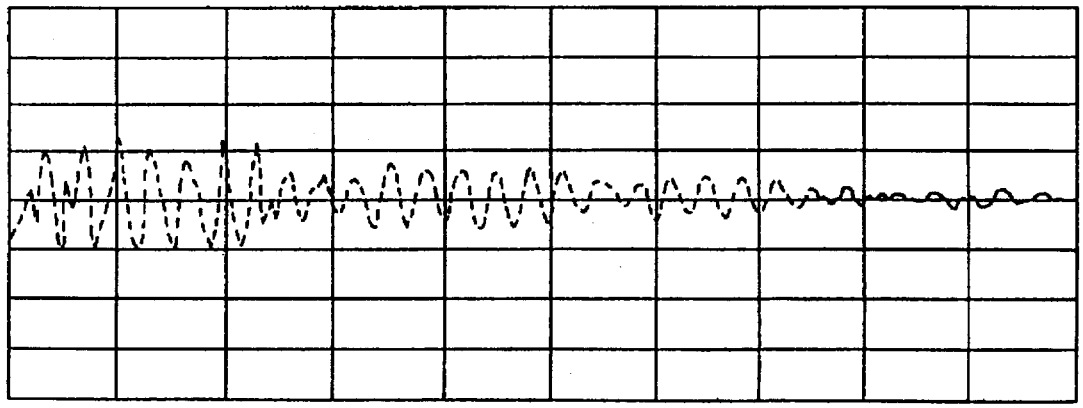
→ TIME
FIG. 7

$f_0 = 4.0$ MHz, $+20$ dBm AT THE SOUND HEAD
$\frac{1}{2} \times f_0$ $\qquad$ $\frac{3}{2} \times f_0$ $\qquad$ $2 \times f_0$
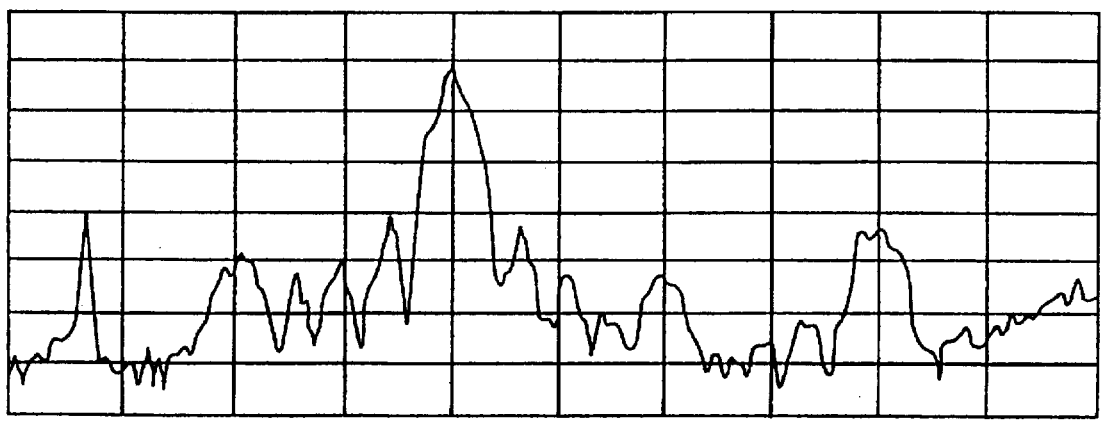
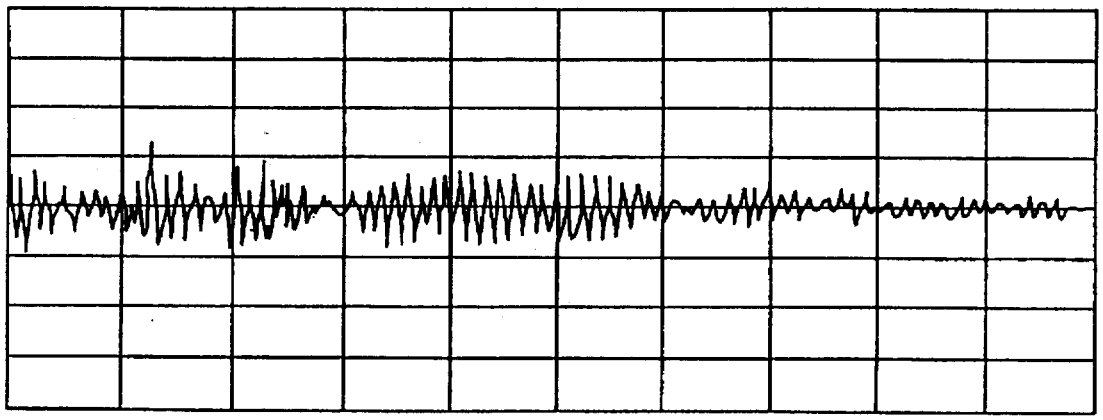
FIG. 8 →TIME $f_0 = 4.0$ MHz, +15 dBm AT THE SOUND HEAD
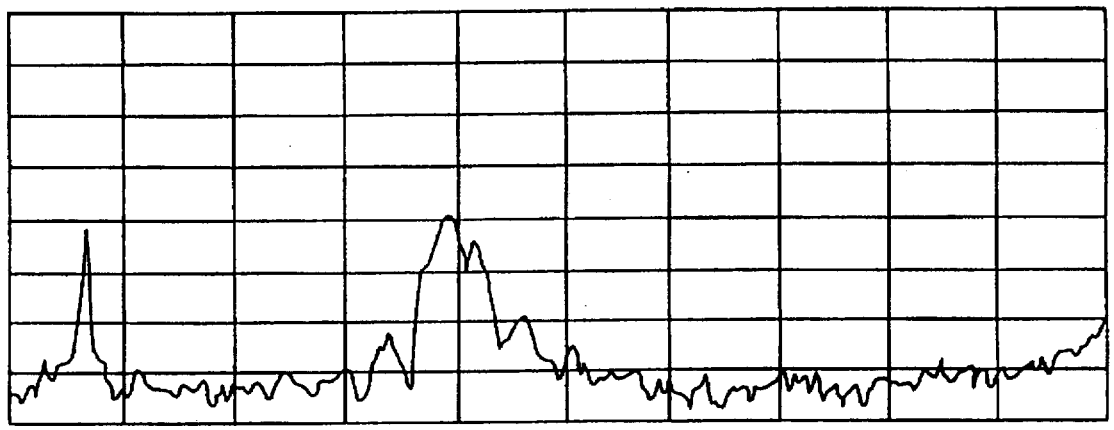
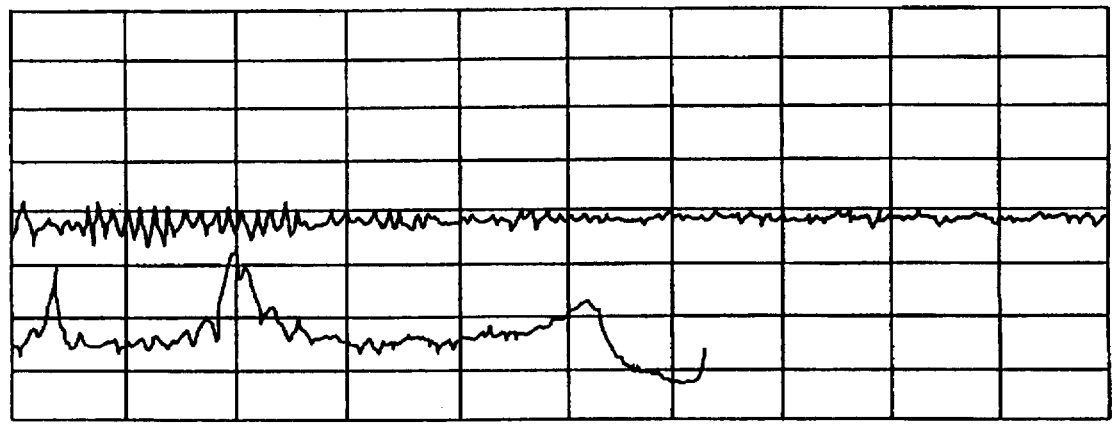
→ TIME
FIG. 9

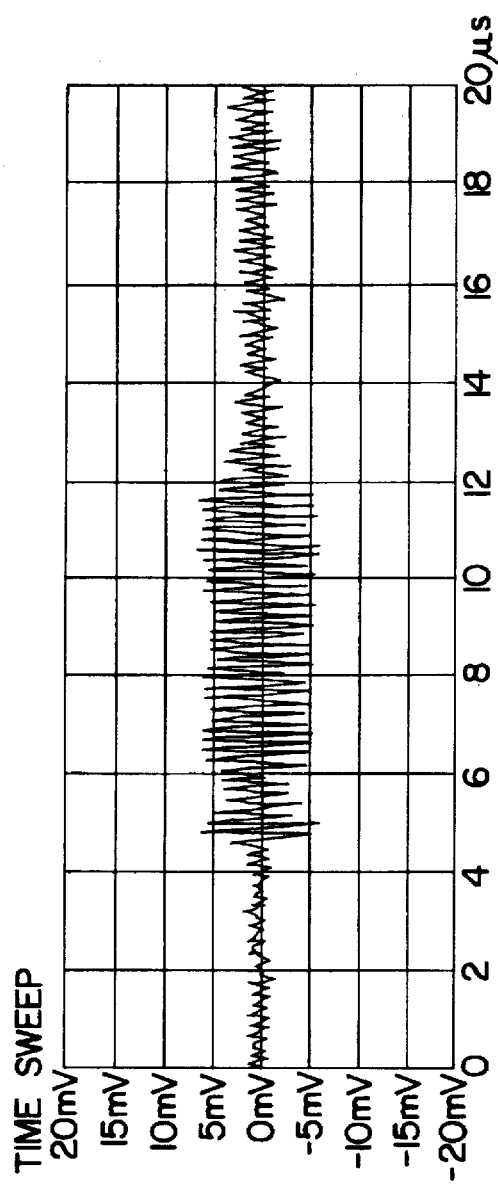
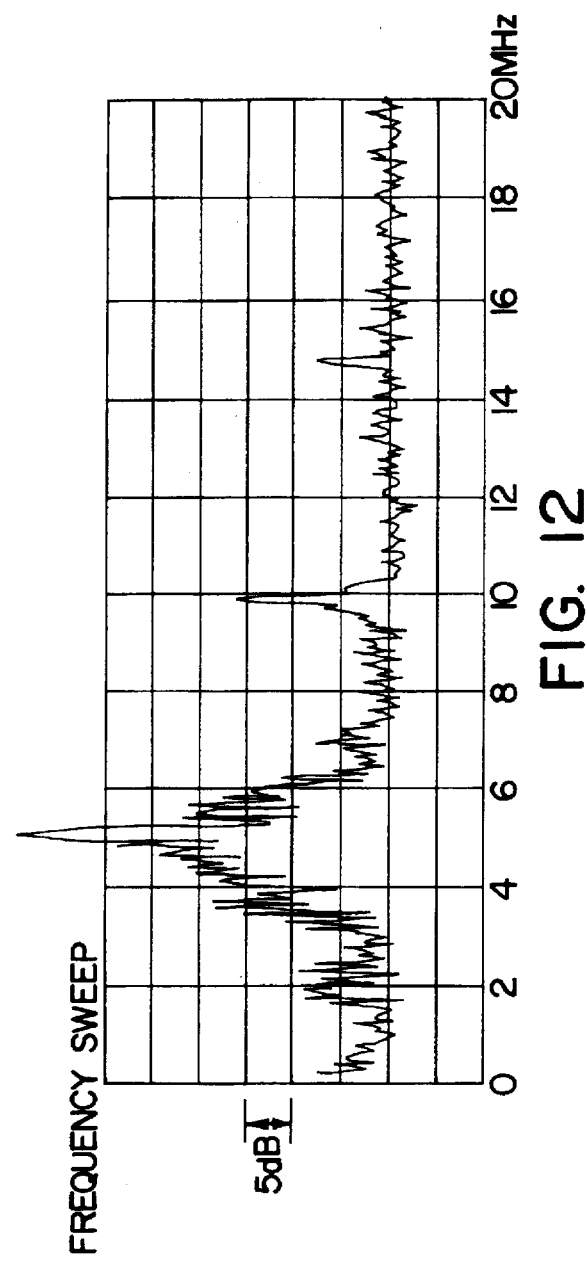
FIG. 12

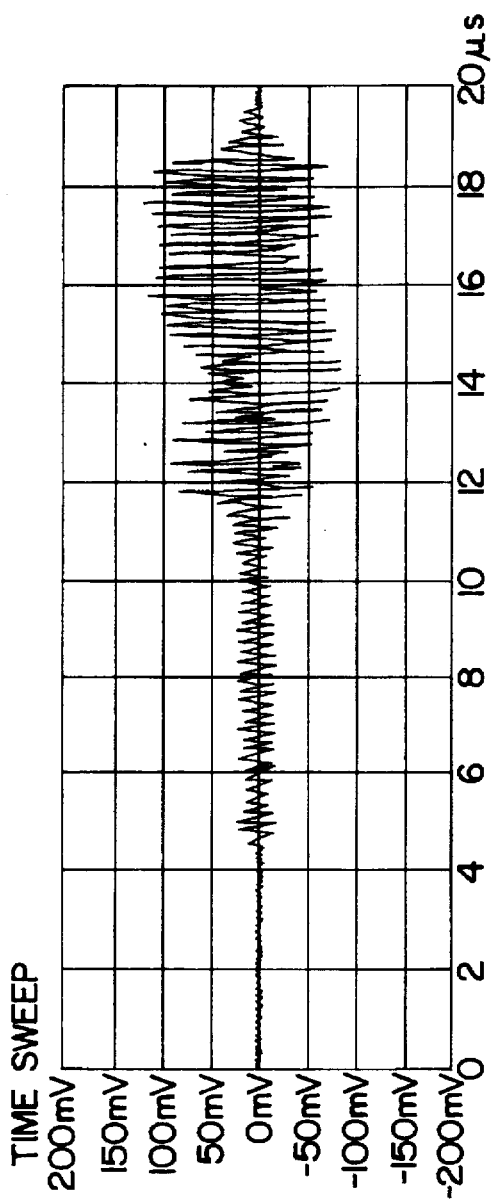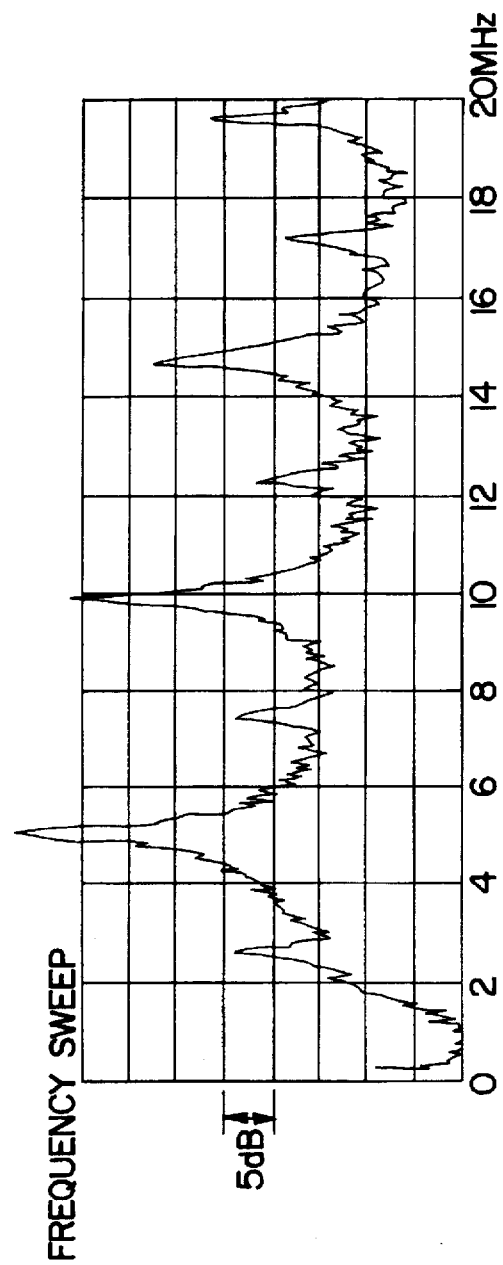
FIG. 13

ULTRASONIC PROCESSES AND CIRCUITS FOR CARRYING OUT THOSE PROCESSES

SUMMARY OF THE INVENTION

The invention relates to ultrasonic processes for imaging and, optionally, for evaluation of a Doppler spectrum of objects having limited resistance to sound intensity, and to circuits for carrying out those processes.

In ultrasonics, ultrasonic waves are radiated into an inspection zone for selective imaging and/or evaluation of the Doppler spectrum. In processes and apparatus for material testing and for examining biological tissue, combined transmitter/receiver sound heads are normally used. By means of the crystals of the oscillators and the apparatus electronics, a sound frequency ($f_o$) is fixed, which is the same for transmitting and receiving. A typical 5 MHz sound head has a frequency range of approximately from 3 to 7 MHz with a maximum at $f_o$=5 MHz. In the case of the pulse echo technique, the reflected and/or backscattered signal is received in the same frequency range. Such apparatus and processes are also employed in the examination of biological tissue using ultrasonic contrast agents. Signal components outside the given frequency range, such as, for example, vibrations that are in a harmonic relationship with respect to the transmission frequency, are not used for imaging the object under inspection and other analyses, such as, for example, Doppler measurements. Furthermore, in order to cover a larger frequency range, the processes and apparatus-systems hitherto known use several sound heads, which are changed during the inspection. EP-A2-0 147 955 discloses an ultrasonic process in which the object to be inspected is exposed to a measuring pulse of high frequency and a pump pulse of low frequency but high sound pressure.

In the evaluation, use is made of the pressure dependence of the sound velocity. The pressure in the object to be inspected is varied by the pump pulse.

The measuring pulse, which is superimposed on the pump pulse, undergoes a phase change, which is ultimately used for the evaluation. The important factor in this known process is therefore the phase relation. There is no evaluation of the harmonic, subharmonic or ultraharmonic frequencies.

In addition, in the known process it is necessary to evaluate a reference signal without a pump pulse in order to be able to measure the phase shift.

A process is known from EP-A3-0 072 330 in which the pressure in the object to be inspected is measured. For that purpose, bubbles are produced in the object under inspection solely by exposure to ultrasonic waves. A low-frequency ultrasonic source in the range below approximately 100 MHz down to, typically, about 20 MHz produces in the object to be inspected, in the low-pressure phase, vapor bubbles in gas-free fluids or, if dissolved gases are present, gas bubbles.

The ultrasonic power is increased until cavitation bubbles form in the body to be inspected. Such bubbles may be very large (easily visible with the naked eye), remain caught in the sound field, and pose a risk of embolism. If they are produced in the tissue, accompanying reactions such as those encountered with decompression sickness are to be expected. Owing to the unavoidable stray low-frequency ultrasonic waves there is a risk especially of lung damage.

EP-A2-0 068 399 describes a process for determining the ultrasonic attenuation or absorption coefficient in tissue. To that end, the variation in the average frequency of the backscatter spectrum in time, or the spatial variation therein in the direction of propagation, is determined. Because of the approximately frequency-proportional attenuation, the average frequency slowly shifts towards lower frequencies as the distance of travel of the pulse of ultrasonic energy increases. The shift from $f_T$ to $f_c$ and $f_R$ is relatively slight.

In the process according to U.S. Pat. No. 3,640,271, blood pressure and flow velocity are measured. For that purpose, individual bubbles of a controlled size within a range of from 10 to 100 μm diameter are injected and their resonant frequency is determined before and after injection. This is effected either with a damped transducer and a frequency sweep, or with a shock excitation from a weakly damped transducer. According to the size of the bubbles, frequencies in the range of from 60 to 600 KHz, that is to say wavelengths of from 2.5 to 25 mm, must be used. The bubbles used are large, so that they are unable to pass through the capillaries. The velocity of the bubbles is measured by means of the Doppler effect or from the time taken to pass between two points.

It is known from literature reference L. Germain, J. O. N. Cheeke, J. Acoust. Soc. Am. 83 (1988) 942, to improve image quality in ultrasonic microscopy using harmonic multiples of the excitation frequency. For that purpose, however, ultrasonic waves of very high amplitude must be radiated in order to produce non-linear vibrations on the way into the inspection zone, energy from the vibrations having the fundamental frequency being converted into higher harmonic vibrations as a result of that non-linearity.

That literature reference, like the literature reference Journal of the Acoustical Society of America, Vol. 69, No. 4, April 1981, pp. 1212, W. K. Law et al., relates to the non-linear propagation of ultrasound, which occurs in water and tissue only at high intensities.

In the case of non-linear propagation, no subharmonic vibrations occur, and harmonic vibrations occur only after a minimum distance of travel of several centimeters in the medium.

However, those processes cannot be used in the ultrasonic inspection, using frequencies, for example, in the range of from 1 to 10 MHz, of objects that are not resistant to high sound intensities, such as, especially, biological tissue.

The problem underlying the invention is to extend the field of application of ultrasonic processes for objects having limited resistance to sound intensity, especially biological tissue, to selective imaging and evaluation of the Doppler spectrum, and to provide circuits for carrying out those processes.

The problem is solved by the instant process.

By introducing materials or media that produce a nonlinearity into the inspection zone to be exposed to low sound intensities, which are not harmful, to obtain, in addition to the excitation frequency, $f_o$, intensive and greatly frequency-shifted scatter and/or transmission signals. These scatter and/or transmission signals are intensive especially at the harmonics (2 $f_o$, 3 $f_o$ ... ), the subharmonics (½ $f_o$, ⅓ $f_o$, ¾ $f_o$) and the ultraharmonics (3/2 $f_o$, 5/4 $f_o$ ... ) of the excitation frequency. With this process, low frequencies can be radiated in, so that a greater depth of penetration is obtained, and received signals of higher frequencies can be evaluated.

In advantageous manner, selective evaluation of the signal components affected by the materials or media which have been introduced and selective representation of the regions filled with those agents are possible without, as was hitherto necessary, finding the difference between two or more conditions recorded before and after application of the materials or media. In particular, the Doppler effect that has been produced can be evaluated free of artifacts.

Advantageously, non-linear scattering bodies are introduced into the inspection zone, but a non-linear ultrasonic contrast agent in the form of a solution or suspension and, especially, microbubbles or agents that produce microbubbles may also be introduced into the inspection zone.

Suitable nonlinear ultrasonic contrast media are, for example, the media, disclosed in EP 0 365 457, incorporated by reference herein, based on galactose particles containing fatty acid.

But under certain conditions—explained in more detail below—contrast media as they are described in DE 38 03 972, WO 93/25242 and WO 94/07539, incorporated by reference herein, are also suitable. These media contain microparticles consisting of a gas core and a polymeric shell and show an ambivalent behavior. At low sonic pressures, they show a linear backscatter behavior, at higher sonic pressures (whose intensity is still in the diagnostic range), a nonlinear backscatter behavior. They can therefore be used according to the invention in the nonlinear range.

The introduction of a microbubble suspension having a concentration of from $10^{-3}\%$ by weight to 30% by weight dry substance in the suspension medium produces good results. The process according to the invention and the circuit according to the invention surprisingly achieve the low bottom limit of $10^{-3}\%$ by weight.

Under certain conditions, especially when using the media described in DE 38 03 972, WO 93/25242 or WO 94/07539, a further increase of sensitivity is possible. These media surprisingly show a superproportional level boosting of the transient backscatter signals with increase in the amplitude of the irradiated signal above a certain threshold value. This superproportional level boosting can be observed not only at the frequency of irradiated signal ($f_o$), but especially also at ½ $f_o$, ⅓ $f_o$, 2 $f_o$, ⁵⁄₂ $f_o$, 3 $f_o$, ⁷⁄₂ $f_o$ and 4 $f_o$. Since the backscatter signal at 2 $f_o$ at supraliminal excitation reaches almost the intensity of $f_o$, this signal is preferably detected. By supraliminal excitation in the diagnostic range, a detection of individual particles or gas bubbles is possible. The dose necessary for a space-filling contrasting can be lowered in the area examined up to a particle (gas bubble) concentration of 10 ppb. Taking into consideration the relative density to 1 ppb, this concentration corresponds to about 1000 particles, preferably 100 to 1000, per cm³ of the body region examined. Also, concentrations of 1000 to 100,000 particles per cm³ may be used.

The reduction of the contrast media concentration results in a decrease of the acoustic damping caused by the contrast medium, by which the penetration depth of the irradiated ultrasonic signal in the tissue is increased. Thus, the sonographic examination of the lower-lying body regions is also possible.

This effect is additionally enhanced in that a destruction of the particles (or bursting of the gas bubbles) is caused by the irradiation of ultrasound with an energy above the above-mentioned threshold value, so that the particle (bubble) concentration in the tissue constantly decreases in the course of the examinations. In this case, first the particles (bubbles) are destroyed, which exhibit the smallest distance to the source of sound. With a progressive examination period, the ultrasonic signal also penetrates subjacent layers, by which a uniform contrasting through all tissue (organ) layers is possible. Since these processes occur especially in the smallest contrast medium concentrations in very short time intervals, a recording of the detected signals by modern data acquisition memory techniques is particularly preferred.

The energy necessary for the destruction of the particles (bubbles) varies as a function of the contrast medium selected. In the case of the contrast media disclosed in EP 0 365 467, the energy must lie above a threshold value of 0.03 MPa, in the case of the contrast media disclosed in WO 93/25242 and WO 94/07539, above a threshold value of 0.1 MPa. The energy necessary for other contrast media can be determined easily by one skilled in the art and generally lies in the range of 0.01 to 1 MPa, and the threshold value increases with increasing stability of the bubbles.

The reduction of the contrast medium concentration, possible by the process according to the invention, further allows the imaging of body regions that are deficient in particles, e.g., those that do not belong to the RES. Thus, the tissue perfusion can be represented, i.a., by the detection of the contrast medium in very fine blood vessels, which by their small cross section are able to take up only small amounts of contrast media (e.g., in the myocardium, liver, kidney, muscles, skin, ocular fundus, lymph vessels, lymph nodes, urinary tracts, tubes, small and large body cavities).

The advantages of the process according to the invention become especially clear if site-, structure- or tissue-specific contrast media are to be detected. Such specific contrast media are disclosed, e.g., in WO 94/07539. Since in specific contrast media, generally only a small part of the administered dose attaches to the desired target tissue (organ), a detection by usual ultrasonic methods is problematical. The detection of these small amounts of contrast medium is possible, however, problem-free, by using the processes and circuits according to the invention, especially if the contrast media are irradiated with an energy above its threshold value.

Based on the drastic increase of sensitivity of the process according to the invention in combination with the above-mentioned contrast media, the imaging of all body regions with the exception of lungs, cartilage areas and bones is thus possible.

To use this special sensitivity of the process according to the invention in combination with one of the contrast media mentioned in patent applications EP 0 365 457, WO 93/25242, DE 38 03 972 or WO 94/07539, excitation frequencies in the range of 1–22 MHz, preferably 2–5 MHz, are used. The necessary sonic pressure amplitudes lie in the range of 0.01–5 MPa, preferably 0.03–0.2 MPa. The HF bursts in this case have 1–50 pulses, preferably 2–8 pulses.

In the process according to the invention, the sound transducer is advantageously excited by means of a function generator by which HF bursts having an adjustable amplitude and an adjustable average frequency ($f_T$) in the range of from 0.3 MHz to 22 MHz, preferably from 1 MHz to 11 MHz, and with from 0.5 to 20 cycles, preferably from 1 to 5 cycles, are generated. It has been found especially advantageous to evaluate frequencies that are lower than the average frequency $f_T$ of the sound transducer (transmitter).

In the evaluation it is advantageous to select at least one time interval by means of a computer-controlled gate circuit and to determine the associated frequency spectrum in analog or digital manner. In so doing, the length of the time window and the number of cycles per burst are adjusted between optimum frequency resolution and optimum spatial resolution.

Using the process according to the invention it is possible, advantageously, to evaluate Doppler effects in the case of harmonics of the excitation frequency and in the case of the mixing products, such as the upper sideband in the case of 2-frequency excitations. This permits the representation of relatively slow flows without interference from vessel wall movements.

Moreover, in the evaluation of harmonic signal components or of signals in the upper sideband, an improved depth of penetration and/or spatial resolution is obtained, which is very advantageous in imaging and in Doppler measurements.

The circuit according to the invention for carrying out the process described above comprises a function generator, the output of which is connected by way of a T/R (transmitter/receiver) switch, which is synchronized by the function generator and downstream of which there is connected a signal processing system, to the oscillator of an acoustically highly damped, electrically matched, wide-band transducer element.

In another embodiment of the circuit, the function generator is connected to the input of a transducer, the output of which is connected to a signal processing system.

In the first-mentioned case, when the T/R switch is switched to "transmit", the burst generated by the function generator is applied to the oscillator of the transducer, and the signal received by the transducer, when the T/R switch is set to "receive", is passed on to the evaluation system. In the second case, the input and the output of the transducer are separate, so that a T/R switch is not required.

It is especially advantageous to use a transducer element, the average frequency $f_T$ of which is greater than the upper limit of the working range. The transducer element is so constructed that the sound intensity it emits, as a function of the frequency, has, in the frequency range below the excitation or average frequency $f_T$, a positive first derivative according to the frequency, which derivative, especially in the working range, is approximately constant, or that the sound intensity itself has a constant value in the working range. Owing to this approximately linear frequency response in the working range, a similar frequency response, especially damping, in the inspection zone exposed to ultrasonic waves can be largely compensated for. As a result of this circuit and the transfer that is used, it is possible to change the frequency used for the inspection without changing the sound head. Moreover, in the evaluation of spectra for material characterization, especially in tissue characterization, the optimum ratio of spatial resolution and frequency resolution can be selected.

The process according to the invention can advantageously be carried out by means of a circuit which has a multi-element transducer with transducer elements that receive signals in phase-delayed manner, in order to carry out a phase-array or a dynamically focused process. In this circuit, the output of a function generator is connected, by way of an n-way signal divider, n computer-controlled time-delay circuits and n T/R switches which are controlled by the function generator or by a computer, to the inputs of n acoustically highly damped, electrically matched, wide-band transducer elements, the outputs of which are connected, by way of n T/R's, each to an m-way signal divider. These m-way signal dividers are each connected, by way of m time-delay circuits and m fixed or variable circuits for frequency band selection, and also by way of a circuit for phase-correct summation and, if appropriate, signal division, to a system for the selective further processing of m frequency bands.

In a further solution to the problem underlying the invention, there is introduced into the inspection zone to be exposed to ultrasonic waves a material by means of which non-linear vibrations are produced in that zone by ultrasonic waves which are radiated in, a wide-band, acoustically highly damped, electrically matched ultrasonic transducer having one or more transducer elements, controllable individually or in groups, is excited by means of two HF bursts, the excitation frequencies of which are different and are less than half the upper frequency limit of the working range, and signal combinations of the two excitation frequencies, especially their sum or difference frequency, are evaluated from the ultrasonic signal received by the ultrasonic transducer, reflected from the inspection zone or scattered back from that zone. For achieving the above-mentioned threshold level, it is preferred that at least one of the two frequencies is provided above the threshold level.

In the above process, the radiating in of two separate signals produces a stronger received signal, the frequency of which is a combination of the frequencies of the signals radiated in, especially the sum or the difference frequency. The sum frequency is of particular interest on account of the higher spatial resolution that can be obtained. In this process, one transducer element can be excited by means of two HF bursts, but it is also possible to excite two separate transducer elements with one HF burst each, the average frequencies of those HF bursts being different and being less than half the upper limit of the frequency of the working range.

On account of the non-linearity produced in accordance with the invention, the use of, for example, two low-frequency signals, e.g. $f_o=f_p=2$ MHz, results in a stronger received signal at $f_o+f_p$, i.e., at approximately 4 MHz, than that obtained when, with the same total power $I_o$, $I_p$, only one transmission signal having the frequency $f_o+f_p$ is used. This phenomenon permits a greater depth of penetration at high observation frequencies.

As materials or media that produce the non-linearity there may be used the same materials and media as are used in the process for evaluating the harmonic frequencies of the excitation frequency. It is possible to use substantially the same circuit elements, with the addition of a second HF generator.

In the case of the circuit having a multi-element transducer, in order to reduce the average power radiated into the inspection zone, the second signal is always emitted in the direction of the first signal and begins approximately 1 to 2 cycles earlier and lasts until the end of the first burst signal. In order to achieve this, the second signal from the second generator is so influenced by suitable time-delay circuits that, after passing through the T/R switch, it passes to the same transducer elements in the sound head and is emitted in the same direction as the first transmission signal. The circuit matrix then receives signals at the sum frequency. The T/R switch is controlled by the second transmission signal, which is of longer duration.

Embodiments of the invention will be explained in the following description, with reference to the Figures shown in the drawings, in which.

Figure 3:
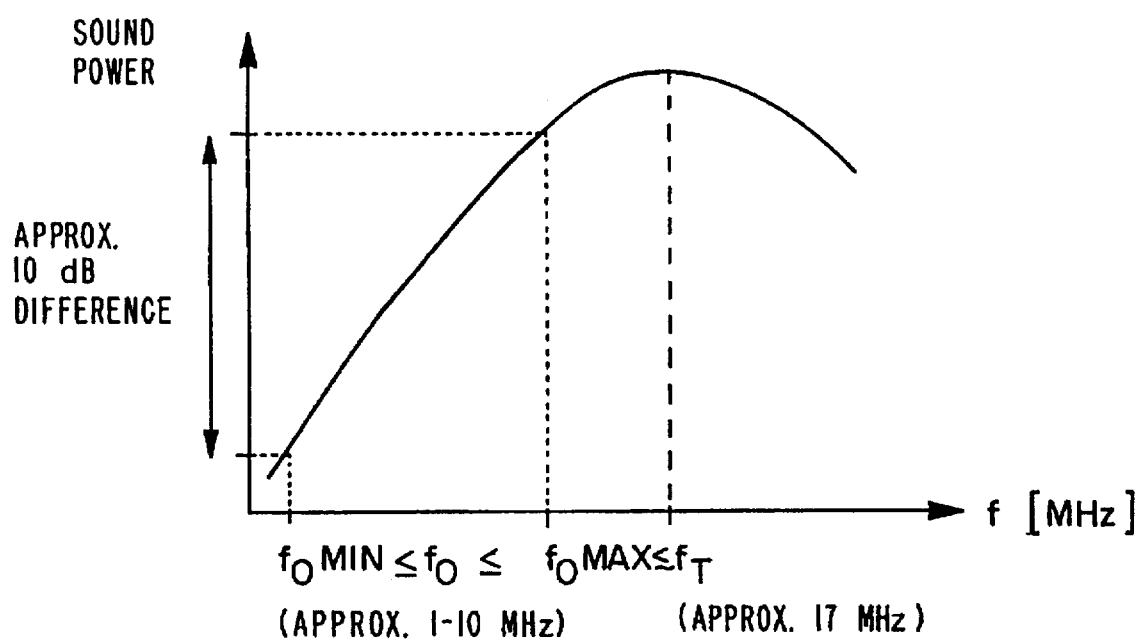
Figure 10:
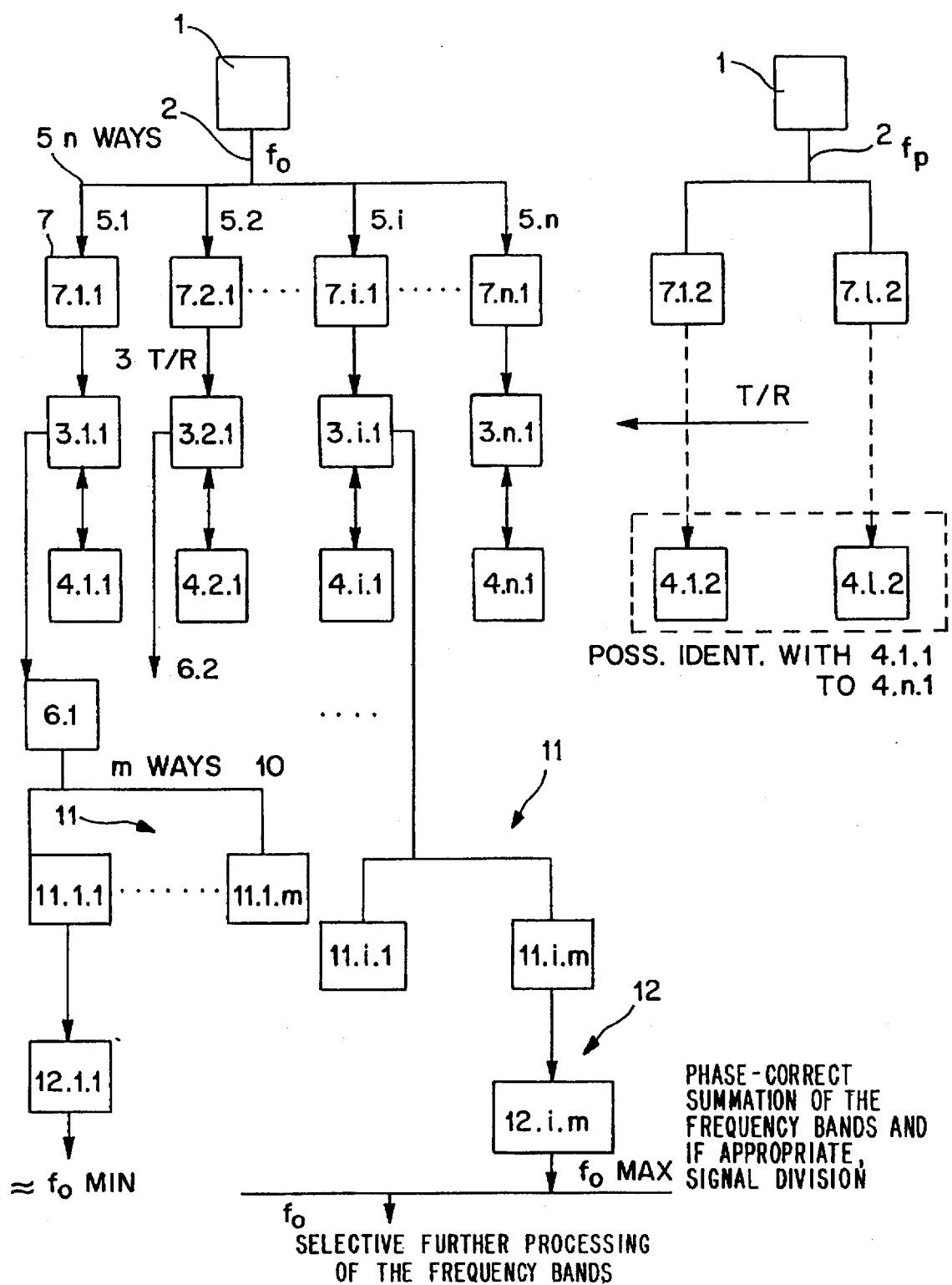
Figure 11:
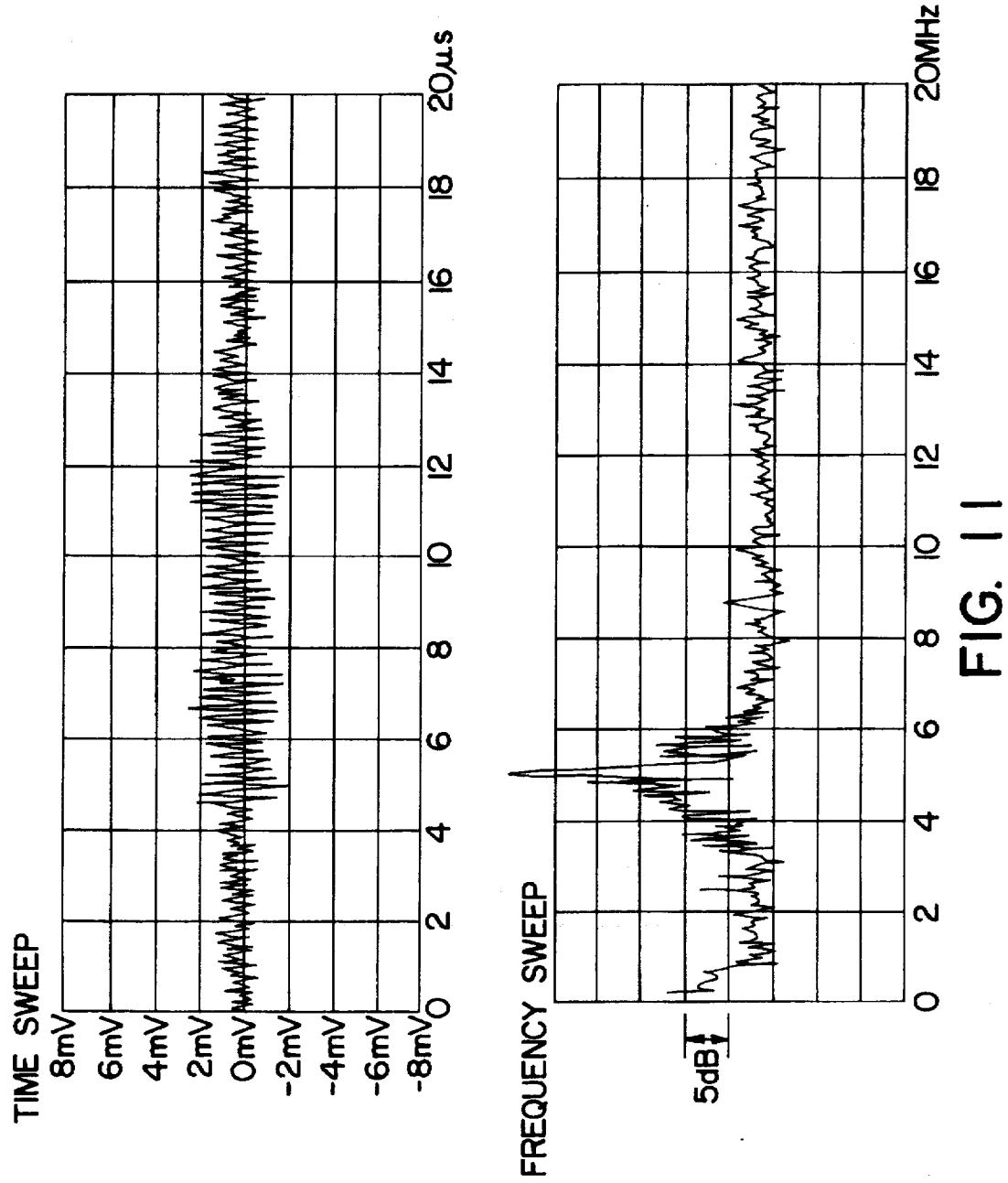

FIG. 3 shows a representation of the sound power curve of the transducer as a function of frequency, FIGS. 4–9 show graphic representations of the backscatter signals, FIG. 10 shows a further block circuit diagram, FIGS. 11–13 Graphic representations of the backscatter signals (time resolution) and their spectra (frequency resolution) at various sound intensities when using a contrast medium as disclosed in WO 93/25242.

Figure 14:
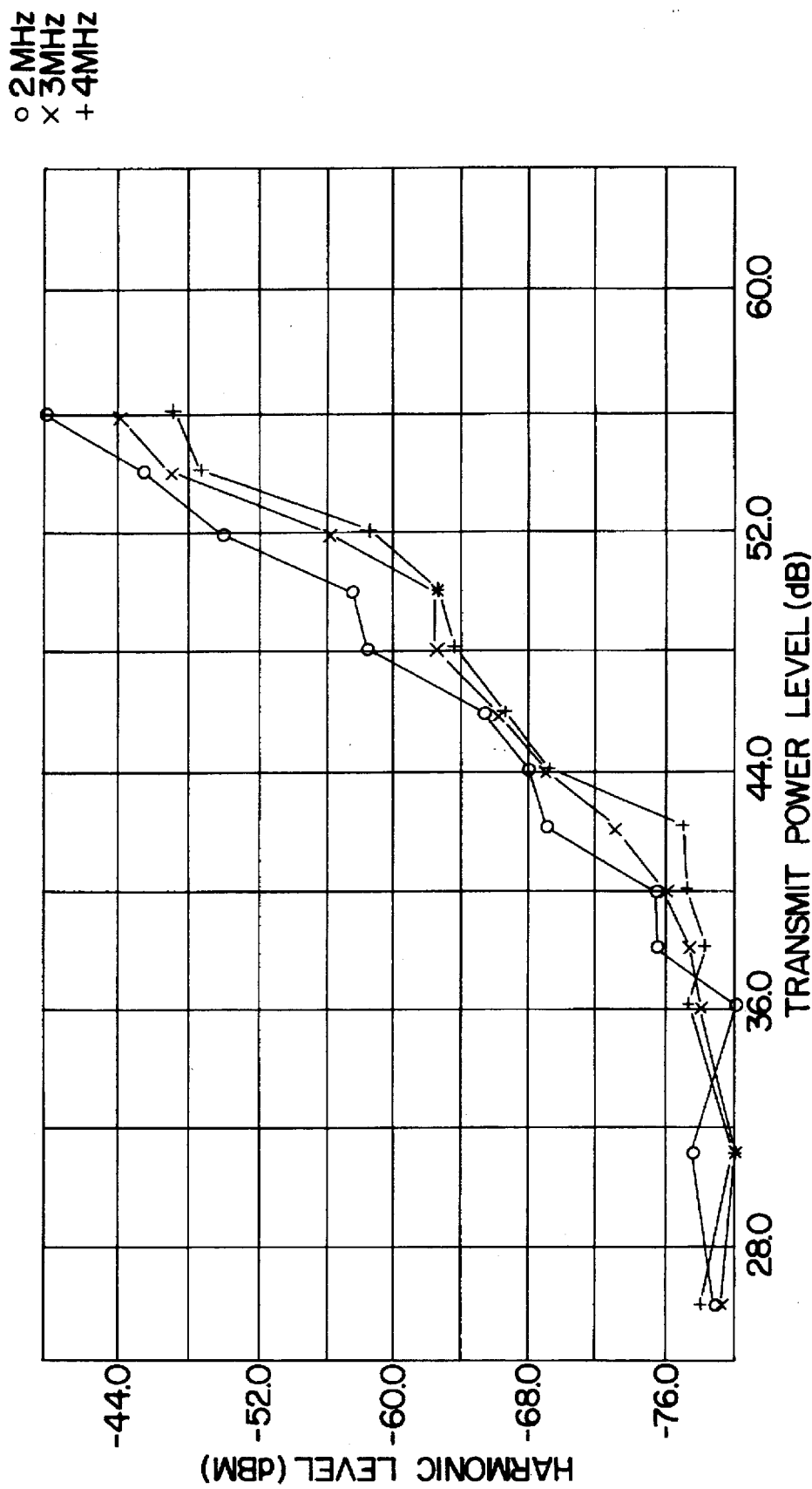

FIG. 14 Graphic representation of the scatter signals at 2 $f_o$ as a function of the sound intensity when using a contrast medium as disclosed in WO 93/25242.

Figure 1:
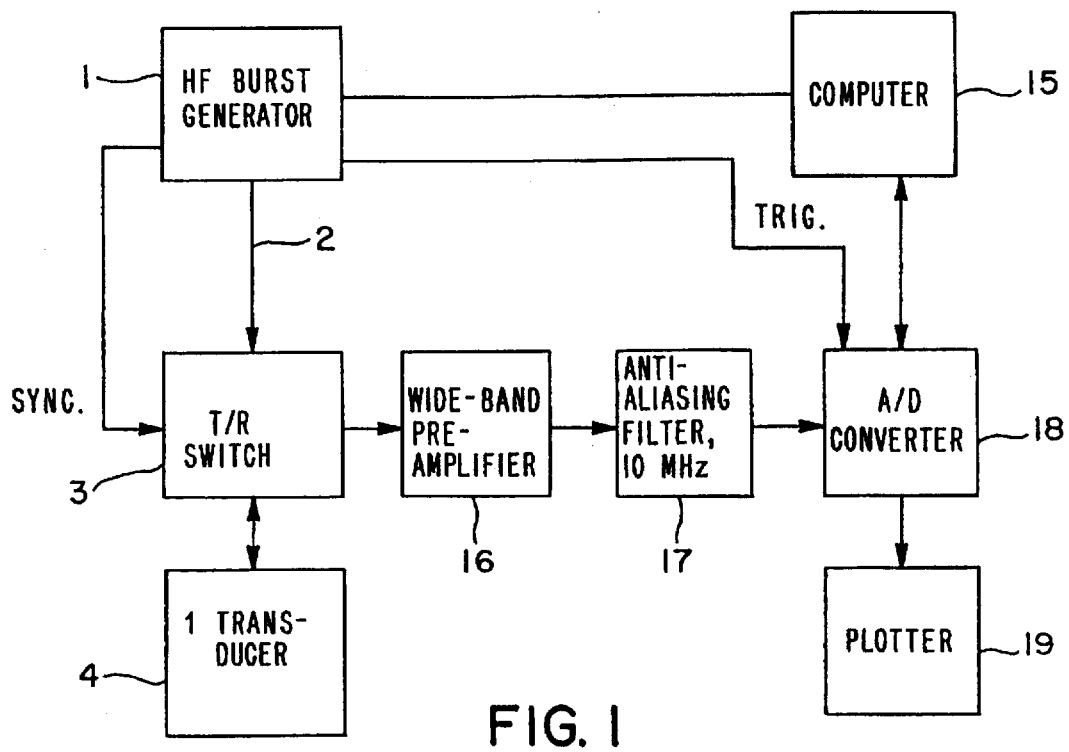
FIG. 1 shows a block circuit diagram.
Figure 2:
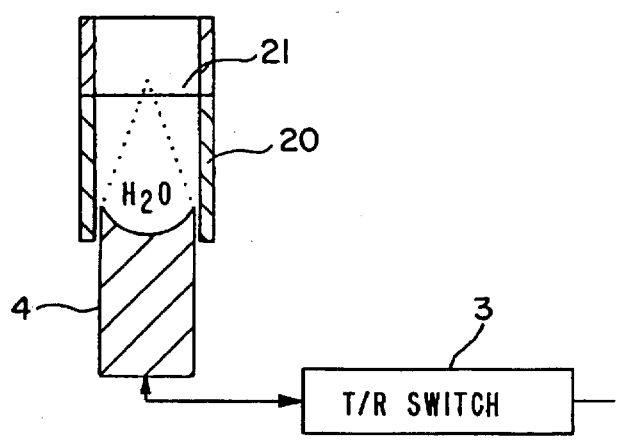
FIG. 2 shows a schematic sectional view of a sample vessel.

To produce the signals shown in FIGS. 4–9, which are ready for further processing, the circuit shown in FIG. 1 is used together with the sample vessel shown in FIG. 2, the wide-band sound head having the power characteristic shown in FIG. 3.

Periodically repeated electrical transmission pulses—HF bursts—of variable frequency $f_o$ in the working range $f_o$ min to $f_o$ max ($f_o$ min=0.3 MHz<$f_o$<$f_o$ max=22 MHz) and of variable bandwidth, given by the number n of sine cycles per burst: 0.5<n<20 with adjustable amplitude, are generated by a function generator 1, which is controlled by the central computer 15. The central computer 15 controls both the course of the measurement and its evaluation. The output 2 of the generator 1 leads to a transmitter/receiver switch 3 which, as shown schematically, is synchronized by the generator 1. The T/R switch 3 may also be controlled directly by the computer 15. The output 2 of the T/R switch 3 is connected to a wide-band, matched and focused transducer element 4. The particular features of the transducer element 4 are shown schematically in FIG. 3. The transducer is a very wide-band transducer without interfering resonances in the working range; furthermore, it has good electrical and acoustic impedance matching and a transmitter average frequency $f_T$>$f_o$ max. In the Example described, $f_T$=17 MHz. The transducer may also have spatially and electrically separate transmitter and receiver transducer elements. In that case the T/R switch 3 is unnecessary. Advantageously, there may also be provided a further transducer element for emitting a second, independent high-frequency signal.

The signal received by the transducer element 4 is fed via the switched-over T/R switch to a wide-band preamplifier 16 downstream of which, in the case of digital frequency analysis, there is connected an anti-aliasing filter 17. The wide-band pre-amplifier 16 has a bandwidth>$f_o$ max. The filter 17 has, for example, a cut-off frequency of 10 MHz. Downstream of the filter 17 there is connected a high-speed A/D converter in which the signal is digitized, for example with a Nyquist frequency of 12.5 MHz. Further processing of the signals is carried out in a digital storage oscilloscope and in the central computer. Downstream of the A/D converter 18 there is connected a plotter 19.

FIG. 1 shows that the A/D converter is triggered by the function generator 1.

The digitized signal is stored and processed further in a manner known, per se. It is available especially for necessary corrections. It is also possible for a signal to be branched off before the A/D conversion and digitized only after analog further processing.

FIG. 2 shows schematically the geometry of vessel 20 with which the measurement results given below were obtained.

As shown in FIG. 2, the sound head 4 is arranged in the sample vessel 20. It is a 17 MHz sound head, which is wide-band, matched and focused. The sample vessel 20 contains water. Two films 21 bound a sample region in which 10 mg of ultrasonic contrast agent are dissolved in 3 ml of $H_2O$.

The reflected and/or backscattered signals in the measurement region between the films 21 contain certain components which were obtained by interaction of the transmission pulse (at $f_o$) and the non-linear contrast agent introduced into the object of measurement.

FIG. 3 shows schematically the frequency band of the transducer element in the sound head. It will be seen that, in the working range, the frequency response of the oscillator in the sound head is quasi-linear. The frequency response in the working range can be used to compensate for a similar frequency response in the sample under examination, but the frequency response in the sample under examination may also be corrected subsequently by weighting.

Figure 4:
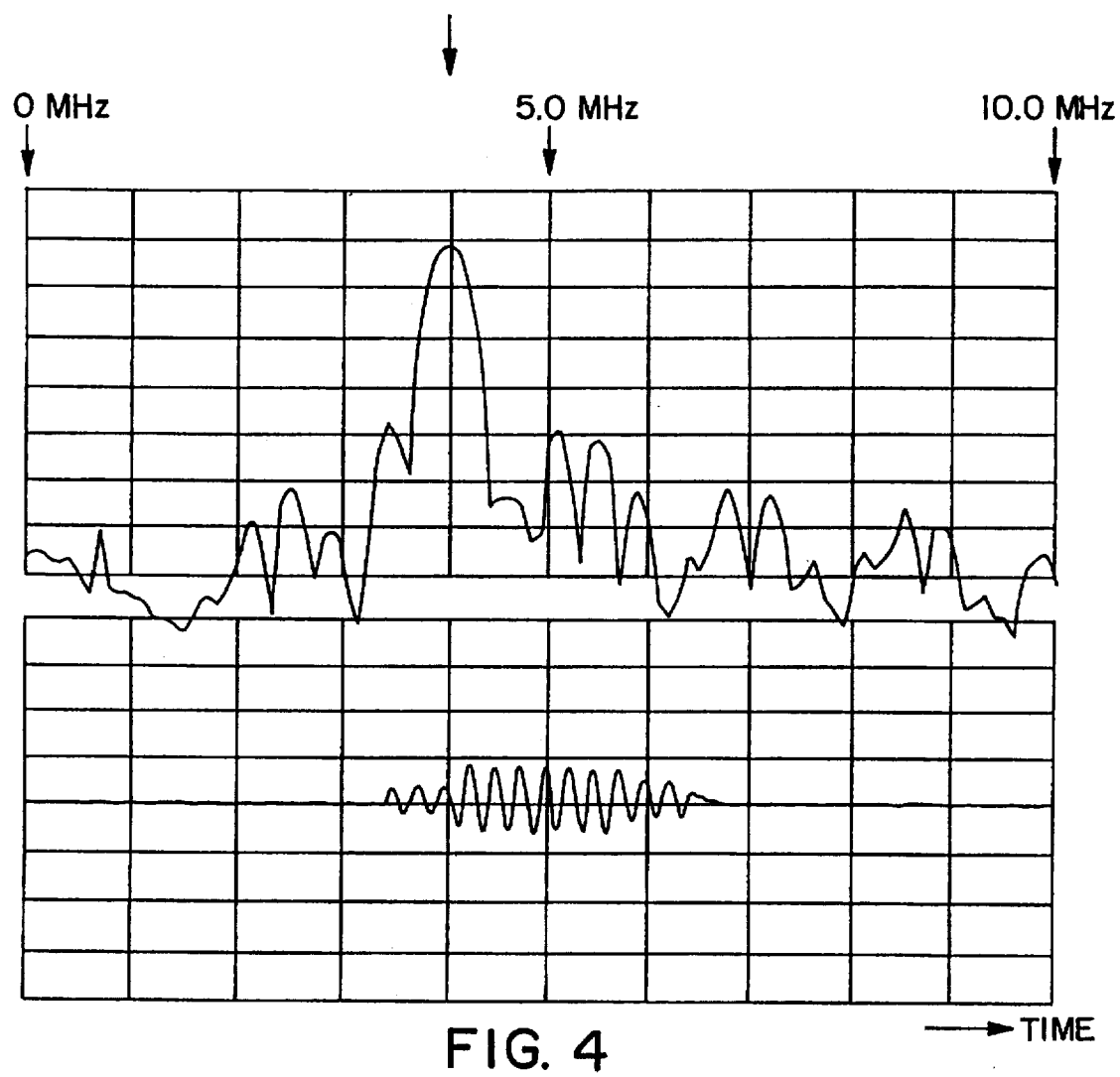

For measurement, an interesting time interval in the time range is selected by means of a computer-controlled gate circuit (not shown). It is also possible to select several time intervals. The associated spectrum is calculated by means of an FFT circuit (Fast Fourier Transformation), and examples of such spectra are shown in FIGS. 4 to 9. By selecting a suitable time window length, it is possible to choose between optimum frequency resolution and optimum spatial resolution. FIGS. 4 to 8 each show the spectrum over the time window. In order to show the spectral components clearly in these Figures, a long time window, that is to say poor spatial resolution, was chosen. FIG. 4 illustrates the variation in time of the transmission pulse after reflection at the coupling window without contrast agents. $f_o$=4.0 MHz, +15 dBm at the sound head. A clear signal can be seen at 4 MHz. The signal shown in the upper part of FIG. 4 is an averaged power spectrum, which was obtained behind the low-pass filter with a Nyquist frequency of 50 MHz.

Figure 5:
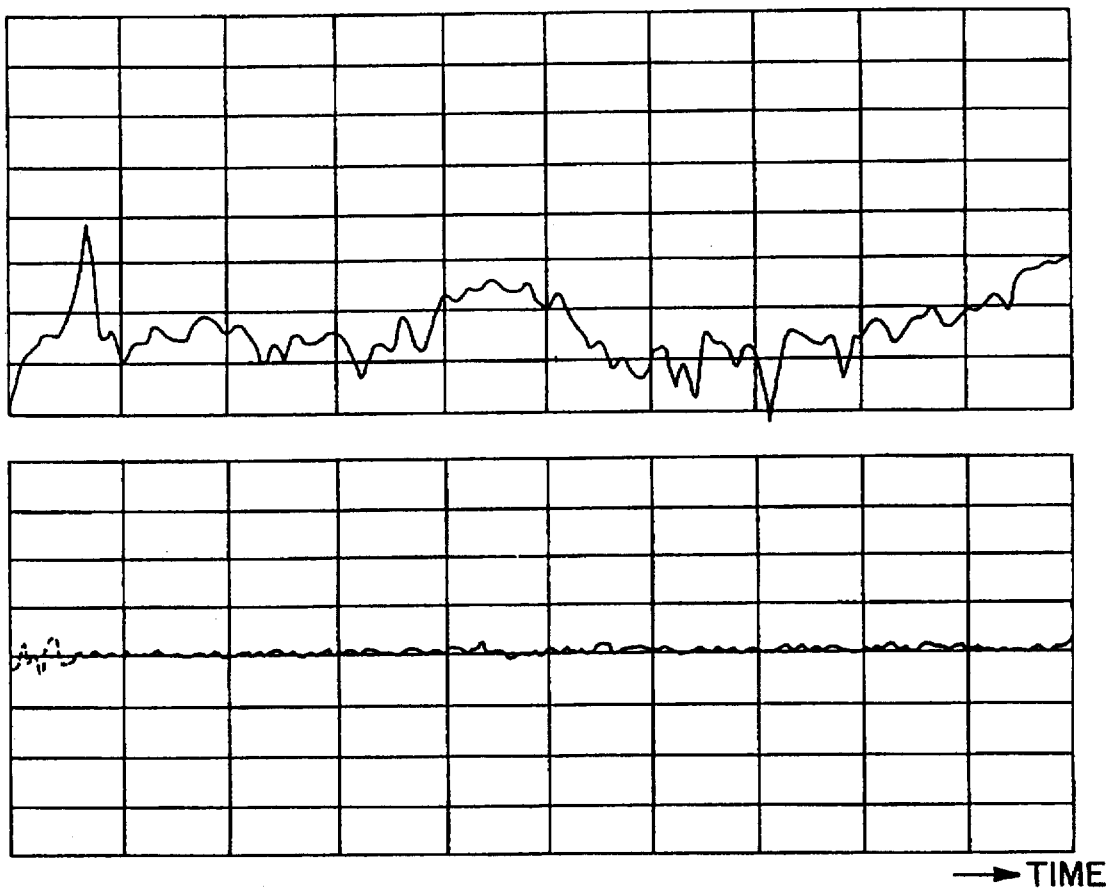

FIG. 5 shows the backscatter signal from the sample chamber without ultrasonic contrast agents. FIG. 6 shows the backscatter signal seven minutes after the addition of 10 mg of contrast agent in 3 ml of $H_2O$. A clear peak can be seen at 2×$f_o$.

FIG. 7 shows a measurement after 21 minutes under the conditions given in FIG. 5. A frequency $f_o$=3 MHz was used. The spectrum recorded clearly shows the first and second harmonics at 6.0 and 9.0 MHz. FIG. 8 shows the backscatter signal 15 minutes after the addition of an ultrasonic contrast agent in a small concentration. A frequency $f_o$ of 4 MHz+20 dBm at the sound head was used. The spectrum shown in the upper part of FIG. 8 shows with relatively high frequency resolution the subharmonic at ½ $f_o$, the ultraharmonic at ³⁄₂ $f_o$ and the first harmonic at 2 $f_o$.

FIG. 9 shows a backscatter signal from linear ultrasonic contrast agent $f_o$=4 MHz+15 dBm at the sound head. The spectrum shows backscattering only at the excitation frequency.

It will be seen that the spectra illustrated have clear amplitudes in frequency ranges that do not occur in the transmitted spectrum when interaction with a non-linear contrast agent has taken place. It is possible to evaluate spectral changes dependent on a Doppler effect. In order to use the circuit employed in the embodiments described for imaging ultrasonic processes, additional components are provided in case a phased-array-type sound head or a dynamically focused sound head is used. Such a circuit diagram is shown in FIG. 10.

The transmission signal from the function generator 1 (frequency $f_o$) is fed from the output 2 to the n-way signal divider 5. The signal is divided to one branch per transducer element. In the embodiment shown, n transducer elements 4 are provided. The transducer elements 4.1 . . . 4.n receive the signal by way of the time-delay circuits 7.1 . . . 7.n and the T/R switches 3.1 . . . 3.n which are controlled by the generator or the computer. The computer sets the time delay for each transducer element in such a manner that, at the selected transmission frequency, the desired directional characteristic is produced at the sound head. The same directional characteristic is set by the computer in the receiver part by corresponding time delays. The signal received by the sound heads 4.1 ... 4.n is fed by way of the T/R switches 3.1 ... 3.n to wide-band pre-amplifiers 6.1 ... 6.n. Each pre-amplifier 6.1 ... 6.n supplies a signal to an m-way signal divider 10, downstream of which are connected suitably controlled or adjusted time-delay circuits 11 which feed circuits 12 for frequency band selection. Connected downstream are circuits for the phase-correct summation of the frequency bands and, if appropriate, for signal division. This is followed by selective further processing of the individual frequency bands by means of processes known per se.

In particular, evaluation of the frequencies that are not identical with $f_o$, for example ½ $f_o$, 2 $f_o$, is carried out.

The time-delay circuits may be variable or fixed. The distribution of the received signals to m-way signal dividers produces the desired number of frequency bands, the position and width of which are adjusted by means of band filters. Alternatively, the division may be effected in such a manner that the received signal is mixed with an auxiliary signal, which is derived from the initial signal-and is different depending on the frequency band, in such a manner that the individual bands can work with uniform components in the subsequent stages.

The frequency band around $f_o$ gives the usual results, while the other bands contain greatly frequency-shifted and non-linear signal components from interaction of the transmission signal with the non-linear ultrasonic contrast agents.

The further processing steps and signal analyses may be carried out in any desired frequency channel or in several parallel frequency channels in accordance with known processes.

In-order to use two transmission frequencies $f_o$ and $f_p$, the second generator, shown on the right-hand side in FIG. 10, is provided, which generator is connected by way of signal dividers and time-delay lines 15 to the T/R switches 3.1 ... 3.n. The second generator 1 allows the exposure to ultrasonic waves of at least that spatial region in the object under examination which is determined by the directional characteristic at the time and the receiver gate. The construction may be such that, in addition to the wide-band transducer elements described, the sound head contains at least one further, likewise wide-band, transmission transducer, which is preferably electrically separate from the others and is fed by the second, independent transmission generator 1. However, the two transmission signals may also be superimposed electrically in such a manner that the same transducer elements can be used.

FIG. 11 (upper half of the figure) shows the backscatter signal, caused by a contrast medium as disclosed in WO 93/55242, with weak excitation with a 5 MHz burst of an amplitude of 0.1 MPa, in the time range.

In the lower half of the figure, the power spectrum of the same signal is reproduced. The signal in excitation frequency $f_o$ (5 HMz) can be seen clearly; harmonic, sub- and ultraharmonic signals are drowned out in static.

FIG. 12 shows the backscatter signal at excitation with an amplitude of 0.34 MPa under otherwise identical test conditions to those for FIG. 11. In this case, the greater backscatter portion of the contrast medium in the time range can be seen clearly. In the frequency resolution, the signals can be detected clearly at 2 $f_o$ and 3 $f_o$.

FIG. 13 shows the backscatter signal at excitation with an amplitude of 1 MPa. The backscatter portion of the contrast medium is, in the time range (upper half of the figure), clearly greater than the reflexes of the transmitting pulse, and it is to be noted that 1 scale mark corresponds to the ordinate here of 50 mV. In the power spectrum (lower half of the figure), the signals can be seen clearly at ½ $f_o$, $f_o$, 3/2 $f_o$, 2 $f_o$, 5/2 $f_o$, 3 $f_o$, 7/2 $f_o$ and 4 $f_o$. Surprisingly, the signal at 2 $f_o$ is of an intensity similar to the echo of irradiated frequency ($f_o$).

FIG. 14 shows the intensity of the backscatter signal at 2 $f_o$ as a function of the irradiated sonic pressure at various excitation frequencies ($f_o$) of 2, 3, and 4 MHz. Also in this case, a contrast medium as disclosed in WO 93/25242 were used. Surprisingly, the intensity of the backscatter detected signal grows above a threshold value of about 40 dB superproportional to the excitation intensity. This behavior is observed in an analogous way also for other contrast medium preparations, e.g., microparticles based on fatty acid-containing galactose particles or microparticles, consisting of a gas core and a biodegradable polymeric shell on which optionally a molecule with site-, structure- and/or tissue-specific properties is bound.

The entire disclosures of all applications, patents, and publications cited above and below are hereby incorporated by reference.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. An ultrasonic process for imaging a body which comprises:
   introducing into the region an ultrasonic contrast medium that contains microbubbles as scattering bodies or that produces microbubbles upon exposure to ultrasonic waves,
   applying an HF burst of excitation frequency, $f_o$, to electrically excite a wide-band, acoustically highly damped, electrically matched ultrasonic transducer having a transducer element or having several transducer elements, controllable individually or in groups, and thereby exposing the region to ultrasonic waves, $f_o$, of 1 MHz to 22 MHz, having an amplitude sufficient to burst at least a portion of the microbubbles in or produced by the contrast medium,
   receiving by the ultrasonic transducer, the ultrasonic signal reflected from the region and scattered back from the region, and processing the received ultrasonic signal for further evaluation, and
   evaluating from the reflected and backscattered ultrasonic signal at least one of the harmonics, the subharmonics and the ultraharmonics of the excitation frequency, $f_o$.

2. The ultrasonic process according to claim 1, wherein the contrast medium is a medium containing
   microparticles based on fatty acid-containing galactose particles, or
   microparticles consisting of a gas core and a biodegradable polymeric shell.

3. The ultrasonic process of claim 2, wherein 1 to 50 pulses are emitted per HF burst.

4. The ultrasonic process of claim 2, wherein 2 to 8 pulses are emitted per HF burst.

5. The ultrasonic process of claim 2 for diagnostic representation of blood vessels.

6. The ultrasonic process of claim 2 for diagnostic representation of capillaries.

7. The ultrasonic process of claim 2 for diagnostic representation of the myocardium.

8. The ultrasonic process of claim 2 for diagnostic representation of the liver.

9. The ultrasonic process of claim 2 for diagnostic representation of the kidney.

10. The ultrasonic process of claim 2 for diagnostic representation of the skin.

11. The ultrasonic process of claim 2 for diagnostic representation of the muscles.

12. The ultrasonic process of claim 2 for diagnostic representation of the ocular fundus.

13. The ultrasonic process of claim 2 for diagnostic representation of the lymph vessels and/or lymph nodes.

14. The ultrasonic process of claim 2 for diagnostic representation of the urinary tract.

15. The ultrasonic process of claim 2 for diagnostic representation of a body cavity.

16. The ultrasonic process of claim 2 for diagnostic representation of the fallopian tubes.

17. The ultrasonic process of claim 16 for the diagnosis of fertility.

18. The process of claim 2, wherein the contrast medium is a medium containing microparticles consisting of a gas core and a biodegradable polymeric shell bound by molecules with site-, structure- and/or tissue-specific properties.

19. The ultrasonic process of claim 1, wherein the excitation frequency, $f_o$, is 2–5 MHz.

20. The ultrasonic process of claim 1, wherein the sonic pressure amplitude is from 0.01 MPa to 5 MPa.

21. The ultrasonic process of claim 1, wherein the sonic pressure amplitude is from 0.03 to 1 MPa.

22. The ultrasonic process of claim 1, wherein the 2 $f_o$ signal is evaluated.

23. The ultrasonic process of claim 1, wherein the inspection zone is a body region and the concentration of microbubbles from the contrast medium in the body region is about 1000 microbubbles per $cm^3$ or less.

24. The ultrasonic process of claim 1, wherein the concentration of microbubbles from the contrast medium in the body region is 1000 to 100,000 microbubbles per $cm^3$.

25. The process of claim 1, further comprising the evaluation of a Doppler spectrum.

26. The process of claim 1, further comprising evaluating the reflected and backscattered ultrasonic signal of the excitation frequency, $f_o$.

27. The process of claim 1, wherein the microbubbles are present in the body region in a concentration of about 100,000 or less microbubbles per $cm^3$ of the body region.

28. An ultrasonic process for imaging a body region which comprises:

introducing into the region an ultrasonic contrast agent that contains microbubbles as scattering bodies or that produces microbubbles upon exposure to ultrasonic waves, applying two HF bursts of excitation frequencies, $f_o$ and $f_p$, to electrically excite a wide-band, acoustically highly damped, electrically matched ultrasonic transducer having a transducer element or having several transducer elements, controllable individually or in groups, wherein the excitation frequencies, $f_o$ and $f_p$, are different and are each less than half the upper frequency limit of the working range of the ultrasonic transducer, and wherein at least one of the excitation frequencies is of effective amplitude to burst at least a portion of the microbubbles in or produced by the contrast medium, receiving by ultrasonic transducer the ultrasonic signal reflected from the region and scattered back from the region, and processing the received ultrasonic signal for further evaluation, and evaluating from the reflected and backscattered ultrasonic signal the sum or the difference of the two excitation frequencies.

29. The ultrasonic process according to claim 28, wherein the contrast medium is a medium containing microparticles based on fatty acid-containing galactose particles, or microparticles consisting of a gas core and a biodegradable polymeric shell.

30. The ultrasonic process of claim 29, wherein 1 to 50 pulses are emitted per HF burst.

31. The ultrasonic process of claim 29, wherein 2 to 8 pulses are emitted per HF burst.

32. The ultrasonic process of claim 29 for diagnostic representation of blood vessels.

33. The ultrasonic process of claim 29 for diagnostic representation of capillaries.

34. The ultrasonic process of claim 29 for diagnostic representation of the myocardium.

35. The ultrasonic process of claim 29 for diagnostic representation of the liver.

36. The ultrasonic process of claim 29 for diagnostic representation of the kidney.

37. The ultrasonic process of claim 29 for diagnostic representation of the skin.

38. The ultrasonic process of claim 29 for diagnostic representation of the muscles.

39. The ultrasonic process of claim 29 for diagnostic representation of the ocular fundus.

40. The ultrasonic process of claim 29 for diagnostic representation of the lymph vessels and/or lymph nodes.

41. The ultrasonic process of claim 29 for diagnostic representation of the urinary tract.

42. The ultrasonic process of claim 29 for diagnostic representation of a body cavity.

43. The ultrasonic process of claim 29 for diagnostic representation of the fallopian tubes.

44. The ultrasonic process of claim 43 for the diagnosis of fertility.

45. The process of claim 29, wherein the contrast medium is a medium containing microparticles consisting of a gas core and a biodegradable polymeric shell bound by molecules with site-, structure- and/or tissue-specific properties.

46. The ultrasonic process of claim 28, wherein the excitation frequency, $f_o$, is 2–5 MHz.

47. The ultrasonic process of claim 28, wherein the sonic pressure amplitude is from 0.01 MPa to 5 MPa.

48. The ultrasonic process of claim 28, wherein the sonic pressure amplitude is from 0.03 to 1 MPa.

49. The process of claim 28, wherein the 2 $f_o$ signal of the at least one excitation frequency is evaluated.

50. The ultrasonic process of claim 28, wherein the inspection zone is a body region and the concentration of microbubbles from the contrast medium in the body region is about 1000 microbubbles per $cm^3$ or less.

51. The ultrasonic process of claim 28, wherein the concentration of microbubbles from the contrast medium in the body region is 1000 to 100,000 microbubbles per $cm^3$.

52. The process of claim 28, further comprising the evaluation of a Doppler spectrum.

53. The process of claim 28, wherein the microbubbles are present in the body region in a concentration of about 100,000 or less microbubbles per $cm^3$ of the body region.

54. An ultrasonic process for imaging a body which comprises:

introducing into the region an ultrasonic contrast medium that contains microbubbles as scattering bodies or that produces microbubbles upon exposure to ultrasonic waves, applying an HF burst of excitation frequency, $f_o$, to electrically excite a wide-band, acoustically highly damped, electrically matched ultrasonic transducer having a transducer element or having several transducer elements, controllable individually or in groups, and thereby exposing the region to ultrasonic waves, $f_o$, of 1 MHz to 22 MHz, having an amplitude at or above a threshold value such that the transient backscatter signals from the contrast media are superproportionally increased in relation to the excitation frequency, receiving by the ultrasonic transducer, the ultrasonic signal reflected from the region and scattered back from the region, and processing the received ultrasonic signal for further evaluation, and evaluating from the reflected and backscattered ultrasonic signal at least one of the harmonics, the subharmonics and the ultraharmonics of the excitation frequency, $f_o$.

55. The process of claim 54, further comprising the evaluation of a Doppler spectrum.

56. The process of claim 54, further comprising evaluating the reflected and backscattered ultrasonic signal of the excitation frequency, $f_o$.

57. The process of claim 54, wherein the microbubbles are present in the body region in a concentration of about 100,000 or less microbubbles per $cm^3$ of the body region.

58. An ultrasonic process for imaging a body region which comprises:

introducing into the region an ultrasonic contrast agent that contains microbubbles as scattering bodies or that produces microbubbles upon exposure to ultrasonic waves, applying two HF bursts of excitation frequencies, $f_o$ and $f_p$, to electrically excite a wide-band, acoustically highly damped, electrically matched ultrasonic transducer having a transducer element or having several transducer elements, controllable individually or in groups, wherein the excitation frequencies, $f_o$ and $f_p$, are different and are each less than half the upper frequency limit of the working range of the ultrasonic transducer, and wherein at least one of the excitation frequencies is of an amplitude at or above a threshold value such that the transient backscatter signals from the contrast media are superproportionally increased in relation to the at least one excitation frequency, receiving by ultrasonic transducer the ultrasonic signal reflected from the region and scattered back from the region, and processing the received ultrasonic signal for further evaluation, and evaluating from the reflected and backscattered ultrasonic signal the sum or the difference of the two excitation frequencies.

59. The process of claim 58, further comprising the evaluation of a Doppler spectrum.

60. The process of claim 58, wherein the microbubbles are present in the body region in a concentration of about 100,000 or less microbubbles per $cm^3$ of the body region.

61. An ultrasonic process for imaging a body region which comprises:

introducing into region an ultrasonic contrast medium that contains microbubbles or that produces microbubbles upon exposure to ultrasonic energy, applying an ultrasonic frequency, $f_o$, of 1 MHz to 22 MHz, having an amplitude effective to burst at least a portion of the microbubbles in or produced by the contrast medium, and evaluating from the reflected and backscattered ultrasonic signal at least one of the harmonics, the subharmonics and the ultraharmonics of the frequency, $f_o$.

62. The process of claim 61, further comprising the evaluation of a Doppler spectrum.

63. The process of claim 61, wherein the microbubbles are present in the body region in a concentration of about 100,000 or less microbubbles per $cm^3$ of the body region.

64. An ultrasonic process for imaging a body region which comprises:

introducing into the region an ultrasonic contrast medium that contains microbubbles or that produces microbubbles upon exposure to ultrasonic energy, applying two ultrasonic frequencies, $f_o$ and $f_p$, which are different and are each less than half the upper limit of the working range of the ultrasonic transducer generating the ultrasonic energy, and wherein at least one of the frequencies, $f_o$ and $f_p$, has an amplitude effective to burst at least a portion of the microbubbles in or produced by the contrast medium, and evaluating from the reflected and backscattered ultrasonic signal the sum or the difference of the two frequencies, $f_o$ and $f_p$.

65. The process of claim 64, further comprising the evaluation of a Doppler spectrum.

66. The process of claim 64, wherein the microbubbles are present in the body region in a concentration of about 100,000 or less microbubbles per $cm^3$ of the body region.

67. A process for imaging a body region, which comprises:

subjecting the body region, having therein an ultrasonic contrast agent comprising microbubbles, to ultrasonic energy of frequency, $f_o$, and amplitude effective to burst at least a portion of the microbubbles and imaging the body region using a harmonic, subharmonic or ultraharmonic of the frequency, $f_o$.

68. The process of claim 67, wherein the microbubbles are present in the body region in a concentration of about 100,000 or less microbubbles per $cm^3$ of the body region.

69. A process for imaging a body region, which comprises:

subjecting the body region, having therein an ultrasonic contrast agent comprising microbubbles, to two different ultrasonic frequencies, $f_o$ and $f_p$, at least one of which is of amplitude effective to burst at least a portion of the microbubbles and imaging the body region using the sum or difference of the frequencies, $f_o$ and $f_p$.

70. The process of claim 69, wherein the microbubbles are present in the body region in a concentration of about 100,000 or less microbubbles per $cm^3$ of the body region.

71. A process for imaging a body region, which comprises:

subjecting the body region, having therein an ultrasonic contrast agent comprising microbubbles, to ultrasonic energy of frequency, $f_o$, and of amplitude effective to superproportionally increase the transient backscatter signals in relation to the frequency, $f_o$, and imaging the body region using a harmonic, subharmonic or ultraharmonic of the frequency, $f_o$.

72. The process of claim 71, wherein the microbubbles are present in the body region in a concentration of about 100,000 or less microbubbles per $cm^3$ of the body region.

73. A process for imaging a body region, which comprises:

subjecting the body region, having therein an ultrasonic contrast agent comprising microbubbles, to two different ultrasonic frequencies, $f_o$ and $f_p$, at least one of which is of amplitude effective to superproportionally increase the transient backscatter signals in relation to at least one of the frequencies, $f_o$ and $f_p$, and imaging the body region using the sum or difference of the frequencies, $f_o$ and $f_p$.

74. The process of claim 73, wherein the microbubbles are present in the body region in a concentration of about 100,000 or less microbubbles per $cm^3$ of the body region.

* * * * *